(12) United States Patent
de la Rama et al.

(10) Patent No.: US 9,572,508 B2
(45) Date of Patent: Feb. 21, 2017

(54) IN-PLANE DUAL LOOP FIXED DIAMETER ELECTROPHYSIOLOGY CATHETERS AND METHODS OF MANUFACTURING THEREFOR

(75) Inventors: Alan de la Rama, Cerritos, CA (US); Jennifer Velasco, Orange, CA (US); Kailing Chen, Laguna Hills, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

(21) Appl. No.: 12/982,618

(22) Filed: Dec. 30, 2010

(65) Prior Publication Data

US 2012/0116199 A1    May 10, 2012

Related U.S. Application Data

(60) Provisional application No. 61/411,694, filed on Nov. 9, 2010.

(51) Int. Cl.
*A61B 18/18*        (2006.01)
*A61B 5/042*        (2006.01)
(Continued)

(52) U.S. Cl.
CPC ........... *A61B 5/0422* (2013.01); *A61B 5/6856* (2013.01); *A61B 18/1492* (2013.01);
(Continued)

(58) Field of Classification Search
CPC ................ A61B 18/1492; A61B 18/24; A61B 2018/00351; A61B 2018/1407; A61B 2018/1435; A61B 2018/00267; A61B 2017/003; A61B 2017/00867; A61N 5/045
(Continued)

(56) References Cited

U.S. PATENT DOCUMENTS 5,263,493 A     11/1993  Avitall
5,628,313 A *    5/1997  Webster, Jr. .................. 600/374
(Continued)

FOREIGN PATENT DOCUMENTS

JP     H9-509069      9/1997
JP     2005-505328    2/2005
(Continued)

OTHER PUBLICATIONS

"International Search Report & Written Opinion", PCT/US2011/059922 Feb. 22, 2012.
(Continued)

*Primary Examiner* — Joseph Stoklosa
*Assistant Examiner* — Brian M Antiskay
(74) *Attorney, Agent, or Firm* — Dykema Gossett PLLC

(57) ABSTRACT

An EP catheter includes a tubular body having a proximal region, a neck region, and a distal portion predisposed into an in-plane dual loop (at least, approximately, more or less) configuration and including a plurality of diagnostic electrodes. In deflectable catheter forms, at least one activation wire extends through at least a portion of the proximal region of the catheter body and is adapted to deflect the distal portion up to approximately 180 degrees relative to the proximal region. The catheter can be operated manually by a clinician or via a clinician-surrogate such as a computer processor-controlled surgical system. In addition, a variety of localization, visualization, and/or orientation-specific elements can be incorporated into the devices described, depicted, and claimed herein (e.g., metallic coil members, active impedance emitting or receiving electrodes, fluoroscopically opaque materials, and the like).

24 Claims, 7 Drawing Sheets

(51) Int. Cl.
*A61B 5/00* (2006.01)
*A61B 18/14* (2006.01)
*B23K 1/00* (2006.01)
*A61B 5/04* (2006.01)
*A61B 17/00* (2006.01)
*A61B 18/00* (2006.01)

(52) U.S. Cl.
CPC ...... *B23K 1/0008* (2013.01); *A61B 2017/003* (2013.01); *A61B 2017/00323* (2013.01); *A61B 2017/00867* (2013.01); *A61B 2018/0016* (2013.01); *A61B 2018/00214* (2013.01); *A61B 2018/00351* (2013.01); *A61B 2018/1435* (2013.01); *A61B 2562/0209* (2013.01)

(58) Field of Classification Search
USPC ........ 600/373–374, 381, 466, 508–509, 585; 606/32–38, 41–42, 45; 607/115–116, 119, 607/122–123, 131
See application file for complete search history.

(56) References Cited

U.S. PATENT DOCUMENTS

| | | | |
|---|---|---|---|
| 5,680,860 A * | 10/1997 | Imran | 600/374 |
| 6,106,522 A * | 8/2000 | Fleischman et al. | 606/41 |
| 6,198,974 B1 * | 3/2001 | Webster, Jr. | A61B 25/0136 600/146 |
| 6,254,568 B1 * | 7/2001 | Ponzi | A61M 25/0144 604/95.04 |
| 6,577,902 B1 * | 6/2003 | Laufer et al. | 607/102 |
| 6,613,046 B1 | 9/2003 | Jenkins et al. | |
| 7,377,906 B2 * | 5/2008 | Selkee | 604/95.04 |
| 7,706,891 B2 | 4/2010 | Hastings et al. | |
| 7,789,877 B2 | 9/2010 | Vanney | |
| 2001/0007070 A1 | 7/2001 | Stewart et al. | |
| 2002/0022839 A1 * | 2/2002 | Stewart et al. | 606/41 |
| 2002/0177765 A1 | 11/2002 | Bowe et al. | |
| 2003/0088244 A1 | 5/2003 | Swanson et al. | |
| 2004/0147827 A1 | 7/2004 | Bowe | |
| 2005/0187455 A1 | 8/2005 | Rashidi | |
| 2006/0241366 A1 | 10/2006 | Falwell et al. | |
| 2006/0247613 A1 * | 11/2006 | White | 606/41 |
| 2007/0270679 A1 | 11/2007 | Nguyen et al. | |
| 2008/0161774 A1 | 7/2008 | Hastings et al. | |
| 2008/0234661 A1 | 9/2008 | Hastings et al. | |
| 2009/0032789 A1 | 2/2009 | Kennedy, Jr. et al. | |
| 2009/0062789 A1 | 3/2009 | Rioux et al. | |
| 2009/0163794 A1 | 6/2009 | Muranushi et al. | |
| 2009/0287210 A1 | 11/2009 | Kauphusman et al. | |
| 2010/0030114 A1 | 2/2010 | Nguyen et al. | |
| 2010/0069733 A1 | 3/2010 | Kastelein et al. | |
| 2010/0168676 A1 | 7/2010 | Datta et al. | |
| 2010/0168827 A1 * | 7/2010 | Schultz | 607/116 |
| 2010/0249568 A1 * | 9/2010 | Stehr et al. | 600/374 |

FOREIGN PATENT DOCUMENTS

| | | |
|---|---|---|
| JP | 2007-518494 | 7/2007 |
| JP | 2010-507403 | 3/2010 |
| WO | 9510318 | 4/1995 |
| WO | 03030713 | 4/2003 |
| WO | 2005070491 | 8/2005 |
| WO | 2006044794 A2 | 4/2006 |
| WO | 2008049084 | 4/2008 |
| WO | 2010048676 A1 | 5/2010 |

OTHER PUBLICATIONS

Atrial Fibrillation Catalog Excerpt, pp. 53-54, Jul. 2007.
Atrial Fibrillation Electrophysiology U.S. Catalog Excerpt, pp. 122-124, St. Jude Medical, 2010.
Jean-Paul Albenque et al, "Atrial Fibrillation Electroanatomical 3D Mapping Optimisation Thanks to a Novel High-density Mapping Catheter—The Inquire AFocus II" Touch Briefings, pp. 63-65, Sep. 2010.
News Release, "St. Jude Medical Showcases Latest Products at Boston Atrial Fibrillation Symposium 2010", Jan. 2010.
"Inquiry AFocus II EB Catheter, Smallest Turning Radius of Any Circular Mapping Catheter", St. Jude Medical, 2010.
"Inquiry AFocusII, Single-Catheter Solution for Streamlined Diagnostics and Mapping", St. Jude Medical, 2009.

* cited by examiner

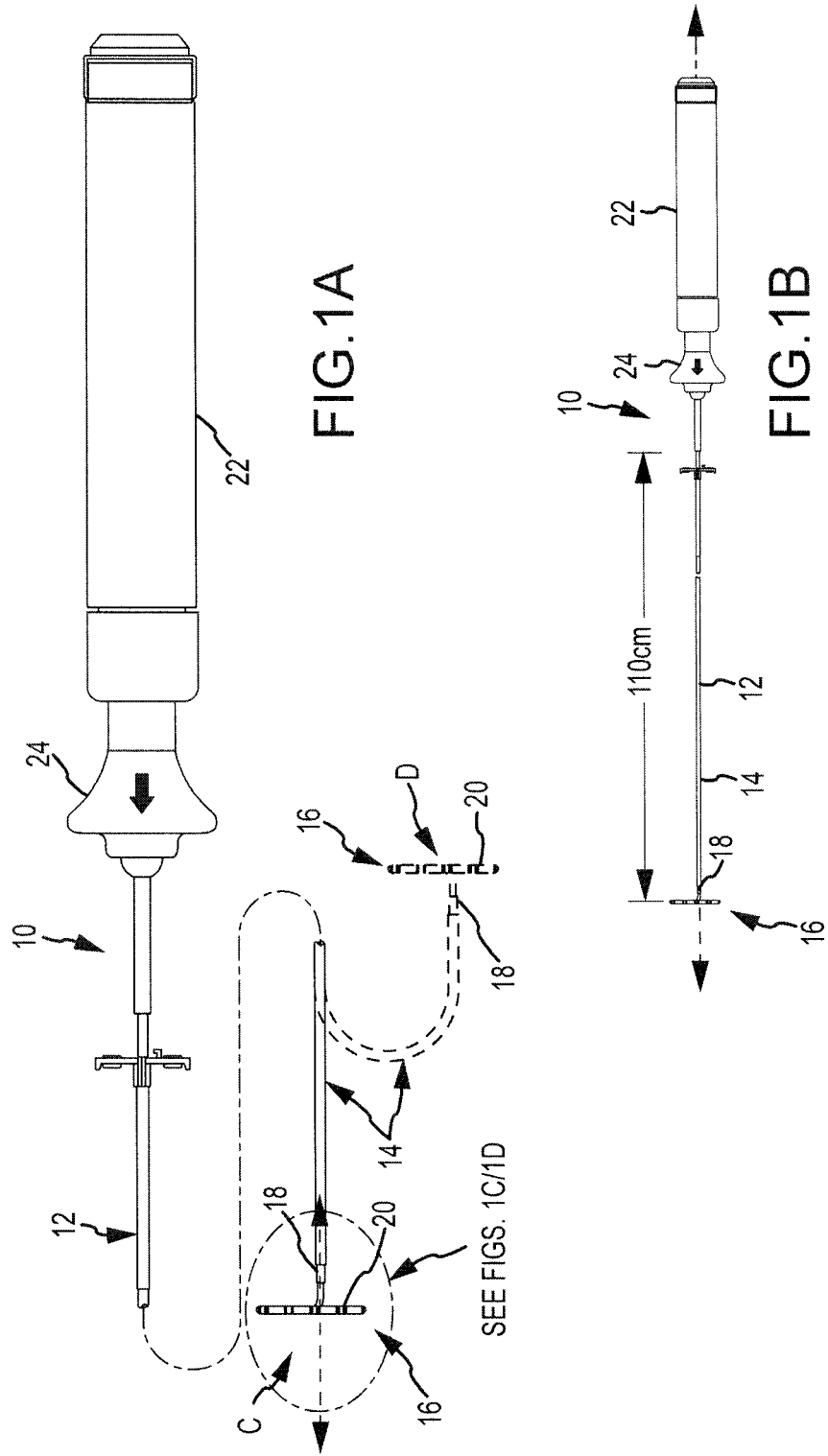

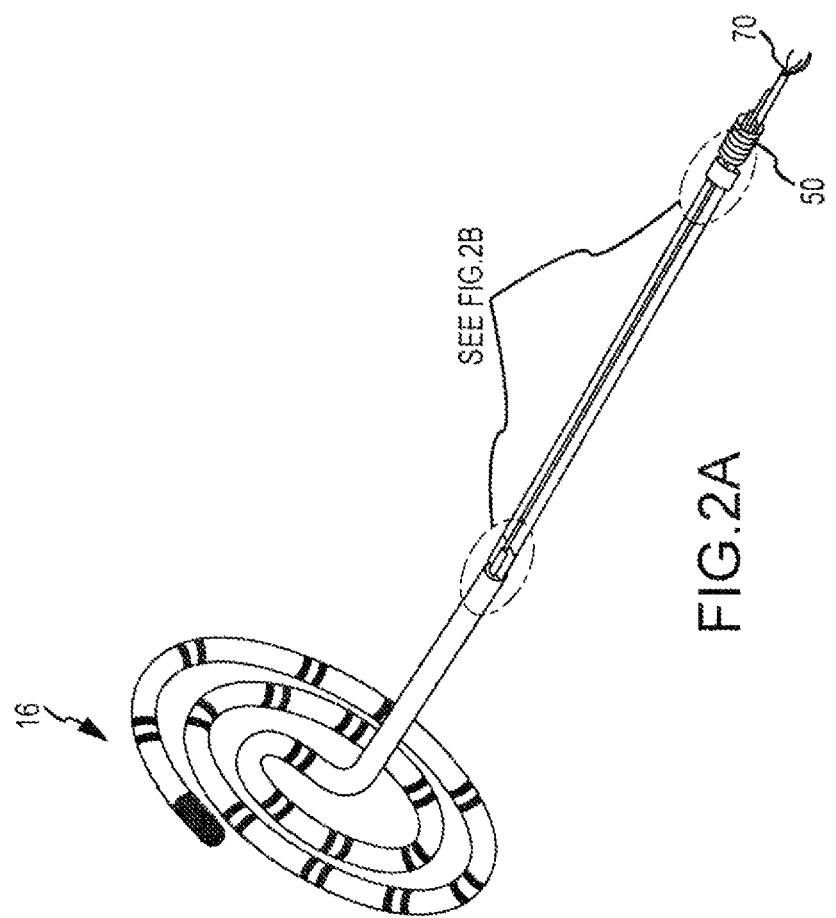

IN-PLANE DUAL LOOP FIXED DIAMETER ELECTROPHYSIOLOGY CATHETERS AND METHODS OF MANUFACTURING THEREFOR

STATEMENT OF INCORPORATION BY REFERENCE

This non-provisional U.S. patent application claims the benefit of and priority to provisional U.S. patent application No. 61/411,694 filed 9 Nov. 2010 (the '694 application), and relates to U.S. patent application Ser. No. 12/760,337 filed 14 Apr. 2010 (the '337 application). The entire contents of the '694 and the '337 applications are hereby incorporated as if fully set forth herein.

BACKGROUND OF THE INVENTION a. Field of the Invention

The disclosure relates to electrophysiology (EP) catheters for use in medical procedures. In particular, the disclosure relates to a family of catheters for use in diagnostic and therapeutic procedures at or near an annular region of a patient's anatomy, such as the ostium of a pulmonary vein.

b. Background Art

Catheters are used for an ever-growing number of procedures. For example, catheters are used for diagnostic, therapeutic, and ablative procedures, to name just a few examples. Typically, the catheter is manipulated through the patient's vasculature and to the intended site, for example a site within the patient's heart.

A typical EP catheter includes an elongate shaft and one or more electrodes on the distal end of the shaft. The electrodes can be used for ablation, diagnosis, or the like. Oftentimes, these electrodes are ring electrodes that extend about the entire circumference of the catheter shaft.

One specific use of an EP catheter is to map the atrial regions of the heart, and in particular the pulmonary veins, which are often origination points or foci of atrial fibrillation. Such EP mapping catheters typically have at least a partial loop shape at their distal end in order to surround the pulmonary vein ostia. Because of varying patient anatomies, however, it can be challenging to properly place the looped section of the catheter precisely in the pulmonary vein ostia.

BRIEF SUMMARY OF THE INVENTION

Accordingly, it is the present disclosure relates to a family of EP catheters having enhanced ability to rapidly collect EP diagnostic data from said subject with a distal portion with a wholly in-plane dual loop relative to other portions of said dual loop.

Another embodiment described and depicted herein relates to EP catheters that allow the in-plane dual loop distal portion to deflect relative to the remainder of the catheter body, thereby permitting the angle of the loop to be fine tuned. In an embodiment, the in-plane dual loop distal portion has an outer-loop diameter of between about 20 mm and about 35 mm, although other dimensions are not excluded. The outer diameter of the catheter body (expressed in units known as French abbreviated as 4 F, for example, each unit of which equals ⅓ of a millimeter, or mm) can vary. For example a majority of the catheter body, the proximal portion, can be on the order of about 7 F and an adjacent neck region can include structure, including an anchoring location for an activation wire, transitions the outer diameter to about 4 F such that the in-plane dual loop distal portion is 4 F or other uniform outer diameter throughout.

In some embodiments, the in-plane dual loop distal portion includes 20 electrodes, including a relatively longer distal tip electrode (e.g., 19 discrete 1 mm wide ring-type electrodes and a single 2 mm long distal tip electrode). In one form, 20 electrodes are distributed in a paired bi-polar mapping configuration wherein each pair is equally separated from each other pair (e.g., 2.5 mm to 7 mm, more or less if desired, apart) and each individual pair is closely situated (e.g., 1 mm apart—including the tip electrode to the most-distal ring-type electrode). Such closely spaced bi-polar pairs tend to reduce so-called far field effects in an in-chamber electrocardiogram (EGM) signal. In another form, 10 discrete electrodes (9 ring-type electrodes and one tip electrode) couple to the in-plane dual loop distal portion to sense EGM signals and are typically evenly-spaced (e.g., 3 mm, 4 mm, 5 mm, 7 mm, or the like) although that is not a requirement as they may be paired in bi-polar pairs as described above. That is, a 1 mm spacing could be following by a 7 mm spacing (in what can be referred to as a 1-7-1 arrangement). In this form the initial spacing between a tip electrode and the next ring-type electrode might be a different value, for example, 2 mm or some other value.

Accordingly, this disclosure describes EP catheters including: a tubular catheter body having a proximal region, a neck region, and a distal portion predisposed into a fixed-diameter loop portion; a plurality of electrodes disposed on the distal portion (e.g., as noted above, 10 or 20—or more or less—also known as deca- and duo-deca pole or polar electrode arrangement—with unipolar and bipolar pairing provided via suitable switching, as desired); a handle joined to the proximal region (for deflecting the distal part of the shaft portion); and a first activation wire extending through at least a portion of the proximal region of the catheter body.

The activation wire deflects the catheter body in a common plane. In general, the activation wire couples to a first element s (e.g., a round or flat wire, a thread of fiber such as Kevlar, or the like) such that forces are transferred to the shaft proximal of the loop (and the neck portion) via a deflection mechanism such as a rotary knob or a push-pull handle as is known in the EP art.

In yet another aspect, the present invention provides a method of manufacturing an EP catheter. The method generally includes the steps of: joining a proximal portion of a shaft portion of an EP catheter to a deflection mechanism and a distal portion to a proximal region of a distal in-plane dual loop region having a plurality of electrodes disposed thereon; joining a manual deflection mechanism including a wire coupled to a distal portion of a segment of flat wire near the neck region and passing through a lubricious tube fastened to the segment of flat wire (thus the flat wire serving as an anchor structure adapted to deflect the proximal portion near the neck region of the EP catheter). A method of delivering therapy via a catheter manufactured according to the foregoing includes: introducing the EP catheter into a patient's body proximate an ostium of interest (in a compressed state); actuating the deflection mechanism to deflect the proximal region of the catheter in order to deflect the catheter, and advancing or otherwise deploying the in-plane dual loop portion relative to the ostium of interest.

An advantage of EP catheters designed, built, and implemented according to the present disclosure is that the distal portion thereof (the in-plane dual loop portion) can be deflected relative to the remainder of the catheter body and thus can efficiently map various surfaces of a heart via the 10 or 20 (or other number) of electrodes.

Thus, an EP catheter according to this disclosure includes a tubular catheter body having a proximal region, a neck region, and a distal portion predisposed into an in-plane dual loop (or greater) configuration and including mapping electrodes arranged in diverse spacings therebetween. In deflectable embodiments, at least one activation wire extends through at least a portion of the proximal region of the catheter body and is adapted to deflect the distal portion (e.g., approximately 180 degrees) relative to the proximal region. The catheter can be operated manually by a clinician or via a clinician-surrogate such as a computer processor-controlled surgical system. In addition, a variety of localization, visualization, and/or orientation-specific elements can be incorporated into the proximal region, neck region, and proximal portion (e.g., metallic coil members, active impedance emitting or receiving electrodes, fluoroscopically opaque materials, and the like) for use in conjunction with an electroanatomical system, for example.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 1A is a plan view including a partially exploded depiction of an exemplary EP catheter having a distal in-plane dual loop cardiac mapping portion with closely-spaced, or high-definition, EP electrodes, with the partially exploded depiction illustrating the catheter in both a deflected and an undeflected configuration.

FIG. 1B is a plan view of the exemplary EP catheter illustrated in FIG. 1A in an undeflected configuration.

FIG. 2A is a close up isometric view of the distal in-plane dual loop cardiac mapping portion of the exemplary EP catheter of FIGS. 1A and 1B (with a perspective view of connecting elements within interior portions of the catheter body, or shaft, illustrated) according to some embodiments of the present invention.

DETAILED DESCRIPTION OF THE INVENTION

Figure 1C:
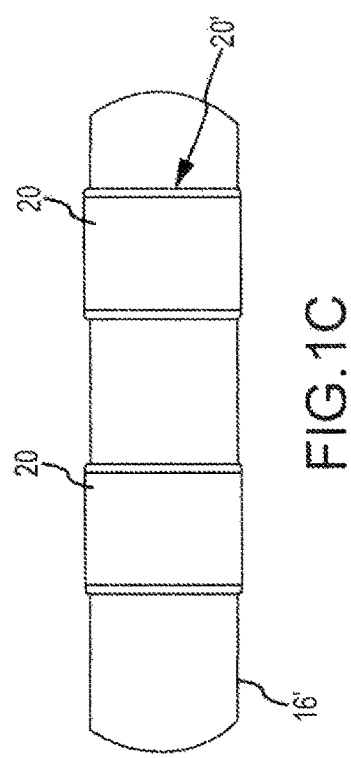
FIG. 1C is an enlarged view of the distal in-plane dual loop cardiac mapping portion of the exemplary EP catheter of FIG. 1A; namely, an illustration of a pair of electrodes residing a segment of the dual loop cardiac mapping portion.

The present invention will be described with reference to an EP catheter utilized in cardiac EP studies, such as the AFocus II DL (or dual loop) diagnostic catheter of St. Jude Medical, Atrial Fibrillation Division, Inc., which can provide relatively faster cardiac activity data collection having the necessary detail to efficiently diagnose complex cardiac arrhythmias. It should be understood, however, that the present teachings can be applied to good advantage in other contexts as well, such as radiofrequency (RF) ablation catheters or other diagnostic cardiac catheters.

Referring now to the drawings, FIGS. 1A and 1B depict an EP catheter 10 according to a first aspect of the present invention.

FIG. 1A is a plan view including a partially exploded depiction of an exemplary EP catheter 10 having a distal in-plane dual loop cardiac mapping portion 16 with EP diagnostic, or mapping, electrodes 20 (as depicted herein arranged in an exemplary duodecapolar configuration), with the partially exploded depiction illustrating the catheter 10 in both a undeflected and a deflected configuration (denoted as "C" and "D" respectively).

FIG. 1B is a plan view of the exemplary EP catheter 10 illustrated in FIG. 1A in an undeflected configuration (i.e., configuration "C" of FIG. 1A).

FIG. 1C is an enlarged view of the distal in-plane dual loop cardiac mapping portion 16 of the exemplary EP catheter 10 of FIG. 1A; namely, an illustration of a pair of electrodes 20 residing on a segment 16' of the dual loop cardiac mapping portion 16. The lateral edges 20' of electrodes 20 are bonded to the adjacent relatively smaller (e.g., 4 F) diameter biocompatible tubing (e.g., PTFE or the like) of portion 16 with a biocompatible material such as a polyurethane matrix composed of Polycin 936 and Vorite 689 (mixed 52:48 percent, as an example) produced by CasChem Inc. of Bayonne, N.J.

Figure 1D:
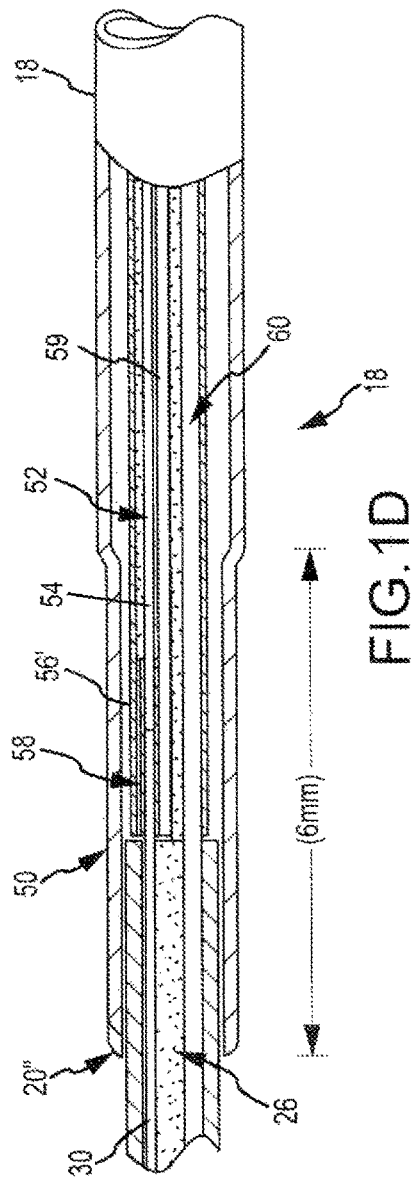
FIG. 1D is an elevational side view in partial cross section of a neck portion formed just proximal of the distal in-plane dual loop cardiac mapping portion of the exemplary EP catheter depicted in FIGS. 1A and 1B.

FIG. 1D is an elevational side view in partial cross section of a neck portion 18 formed just proximal of the distal in-plane dual loop cardiac mapping portion 16 of the exemplary EP catheter 10 depicted in FIGS. 1A and 1B. As shown, an extended braid tube/spring assembly 50 surrounds a variety of subcomponents of catheter 10 and is itself wrapped by a relatively smaller diameter biocompatible tubing 18 that covers the neck region and transitions the outer diameter to the about 4 F distal in-plane dual loop cardiac mapping portion 16. Where the extended braid tube/spring assembly 50 terminates at its distal edge a small amount of medical grade adhesive polymer 20" (e.g., like the polymer 20' used at the edges of electrodes 20) can be applied. A polyimide tube 56' passes through the extended braid tube/spring assembly 50 (and neck region 18) and into the distal in-plane dual loop cardiac mapping portion 16 and isolates a plurality of elongate conductive strands 70' (shown in FIG. 4B) that couple the electrodes 20, 46 to remote circuitry via a handle (22 as shown in FIGS. 1A and 1B) having a mass termination where the conductors 70 pass through the handle to couple to an EP recording system or other diagnostic equipment, for example. A flat wire subassembly 52, which includes segment of flat wire 59, is coupled to an activation wire 54 and is adapted to impart and release tension to deflect the proximal end 16 in a plane defined by the flat wire subassembly 52 (via manipulation of the handle, such as by rotation or linear actuation members, and the like). A short segment of polyimide tubing 56' surrounds a junction of several components; namely, a lubricous tubing member 58 (e.g., PEEK tubing) that receives a proximal end of an elongate shape memory member 30 (formed of nitinol, for example) that is preformed into a desired dimension and configuration for distal portion 16. In one embodiment, the distal portion 16 has an overall outer diameter of 20 mm (i.e., for the outermost loop) with a 4 F dimension for portion 16' and 1 mm (wide) platinum electrodes 20 and a 2 mm (long) tip electrode 46. In this embodiment, the electrodes 20 can be spaced apart in bipolar pairs or evenly (e.g., about 1 or 2-4 mm or other nominal spacing between them). In a bipolar pair configuration the electrode spacing can vary, of course, although in on embodiment the spacing for 1 mm (wide) ring-type electrodes is 1 mm per bipolar pair with 2.5 mm between pairs. In this embodiment the spacing between the tip electrode 46 to the most distal ring-type electrode 20 can also be 1 mm. In the embodiments depicted herein the diameter of the outer loop of the distal portion 16 is fixed (e.g., at about 20 mm or less to about 33 mm or more, if desired) although using reasonably well-known techniques the diameter can be manually varied with one or more tension elements for imparting and releasing tension. Such element(s) couple to structure within one or more locations with a distal looped portion (e.g., using KEVLAR fibers, metallic or composite wires or axially rigid elements, thin so-called pull wires and the like). At the junction of the flat wire subassembly 52 with the nitinol wire 30 wrapped in, for example, PEEK tubing urethane adhesive (denoted by reference numeral 26 in FIG. 2B) can be applied between, above, and around the components within the polyimide tubing 56' to encapsulate same. Similarly, urethane adhesive 26 can be impregnated into the interstices of the neck region 18 and distal portion 16 to reduce or eliminate any migration of the nitinol wire 30 or PEEK tubing 58 or polyimide tube 60 (surrounding conductor 70') during use.

In general, EP catheter 10 can include an elongate catheter body 12, which, in some embodiments, is tubular (e.g., it defines at least one lumen therethrough). Catheter body 12 includes a proximal region 14, a distal portion 16, and a neck region 18 between proximal region 14 and distal portion 16. One of ordinary skill in the art will appreciate that the relative lengths of proximal region 14, distal portion 16, and neck region 18 depicted in FIGS. 1A and 1B are merely illustrative and can vary without departing from the spirit and scope of the present invention but likely should not have a magnitude of less than about 110 cm. Of course, the overall length of catheter body 12 should be long enough to reach the intended destination within the patient's body.

Catheter body 12 will typically be made of a biocompatible polymeric material, such as polytetrafluoroethylene (PTFE) tubing (e.g., TEFLON® brand tubing). Of course, other polymeric materials, such as fluorinated ethylene-propylene copolymer (FEP), perfluoroalkoxyethylene (PFA), poly(vinylidene fluoride), poly(ethylene-co-tetrafluoroethylene), and other fluoropolymers, can be utilized. Additional suitable materials for catheter body 12 include, without limitation, polyimide-based thermoplastic elastomers (namely poly(ether-block-amide), such as PEBAX®), polyester-based thermoplastic elastomers (e.g., HYTREL®), thermoplastic polyurethanes (e.g., PEL-LETHANE®, ESTANE®), ionic thermoplastic elastomers, functionalized thermoplastic olefins, and any combinations thereof. In general, suitable materials for catheter body 12 can also be selected from various thermoplastics, including, without limitation, polyamides, polyurethanes, polyesters, functionalized polyolefins, polycarbonate, polysulfones, polyimides, polyketones, liquid crystal polymers and any combination thereof. It is also contemplated that the durometer of catheter body 12 can vary along its length. In general, the basic construction of catheter body 12 will be familiar to those of ordinary skill in the art, and thus will not be discussed in further detail herein.

Referring now to FIG. 2A which is a close up isometric view of the distal in-plane dual loop cardiac mapping portion 16 of the exemplary EP catheter 10 of FIGS. 1A and 1B (with a perspective view of connecting elements within interior portions of the catheter body, or shaft, illustrated) according to some embodiments of the present invention. As illustrated, the proximal and distal ends of the flat wire subassembly 52 (e.g., implemented to promote planarity during deflection) are emphasized.

Figure 2B:
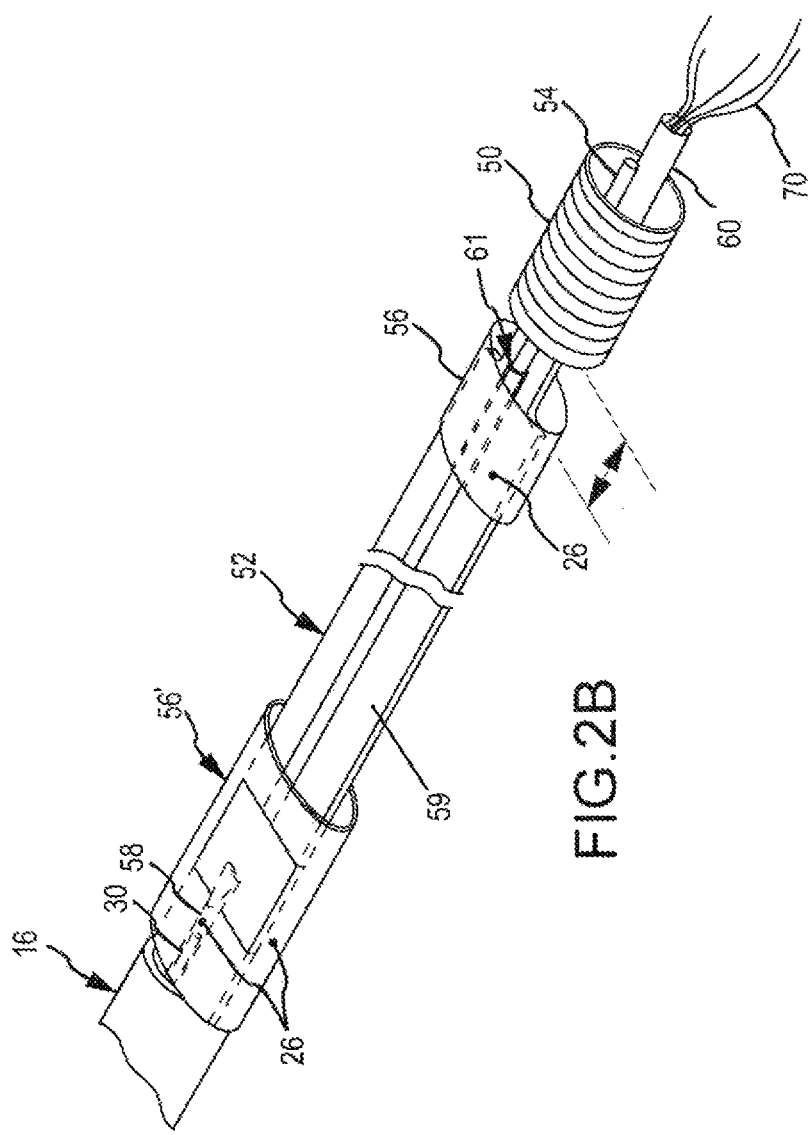
FIG. 2B is an enlarged isometric fragmented view of the interior details of the ends of the connecting elements within the interior of the catheter body shown in FIG. 2A.

FIG. 2B is an enlarged isometric fragmented view of the interior details of the ends of the various connecting elements within the interior of the catheter body 14,18 of FIG. 2A. As depicted, the proximal end of a flattened PEEK tube 58 that contains the nitinol wire 30 is adhered with urethane adhesive 26 (or other suitable medical grade adhesive) to segment of flat wire 59 of the flat wire subassembly 52 and wrapped in polyimide tubing 56' for containment. The proximal end of the flat wire subassembly 52 couples via a segment of polyimide tubing 56 filled with urethane adhesive 26 that also encapsulates the smaller diameter polyimide tubing 61 where the activation wire 54 resides. A gap of about 1-2 mm between the tubing 56 and the distal end of extended braid/spring subassembly 50 should be optionally maintained (as depicted) and the activation wire 54 and conductor wires 70 (within polyimide tube 60) are conveyed through subassembly 50 to a handle or other remote location.

Figure 2C:
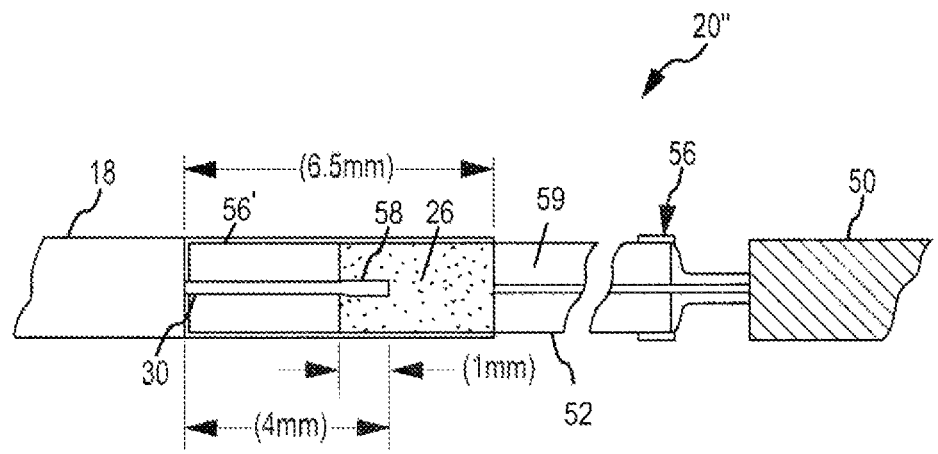
FIG. 2C is an enlarged fragmented plan view of the interior details of the ends of the connecting elements within the interior of the catheter body shown in FIG. 2A.

FIG. 2C is an enlarged fragmented plan view of the interior details of the ends of the connecting elements within the interior of the catheter body shown in FIG. 2A. As depicted, the flattened section of the PEEK tubing 58 disposed within the polyimide tubing 56' can comprise a 1 mm segment to promote adhesion to the urethane adhesive 26 impregnated therein and thus to the flat wire subassembly 52, including segment of flat wire 59. Similarly, the proximal end of the flat wire subassembly 52 can be surrounded by polyimide tubing 56 and impregnated with urethane adhesive (70 not shown) to promote mechanical coupling to the adjacent extended braid/spring subassembly 50. A suitable biocompatible compound 20" (e.g., such as polymer 20') can be applied to the junction between the outer covering for distal portion 16' and the neck region 18.

Figure 3:
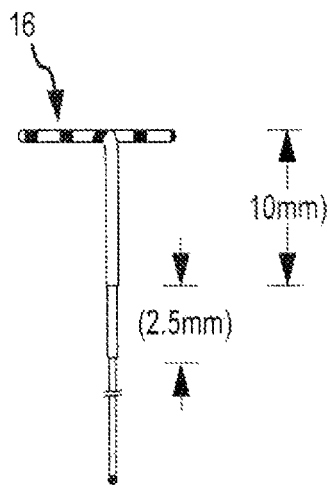
FIG. 3 is an elevational view showing exemplary dimensions of the distal in-plane dual loop cardiac mapping portion of the exemplary EP catheter of FIGS. 1A and 1B according to an embodiment of the present disclosure.

FIG. 3 is an elevational view showing exemplary dimensions of the distal in-plane dual loop cardiac mapping portion 16 of the exemplary EP catheter 10 of FIGS. 1A and 1B according to an embodiment of the present disclosure. For example, the plane of the distal portion 16 can be on the order of 10 mm to the neck region 18, although other dimensions can be used if desired. Whatever dimension is used the wire support length therefrom should be a reasonable length (e.g., 2.5 mm as depicted).

Figure 4A:
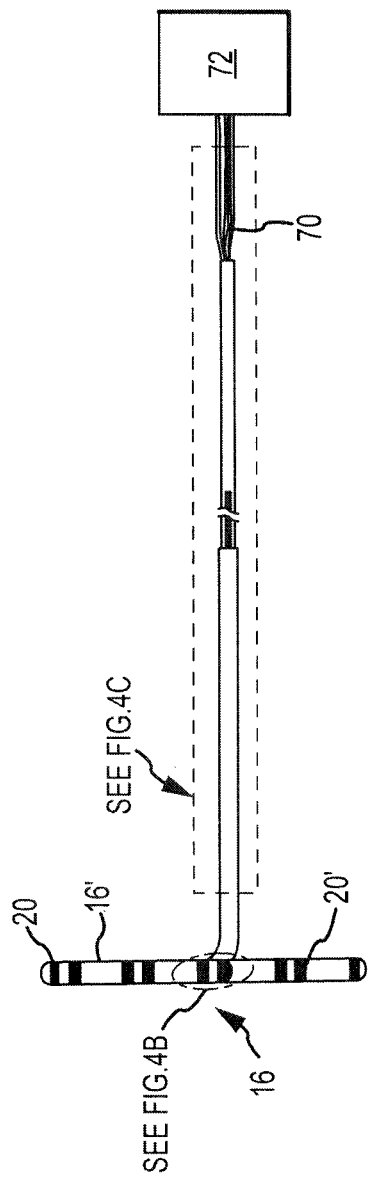
FIG. 4A depicts the distal in-plane dual loop cardiac mapping portion of the exemplary EP catheter of FIGS. 1A and 1B (with cross references to details shown in FIGS. 4B and 4C).
Figure 4B:
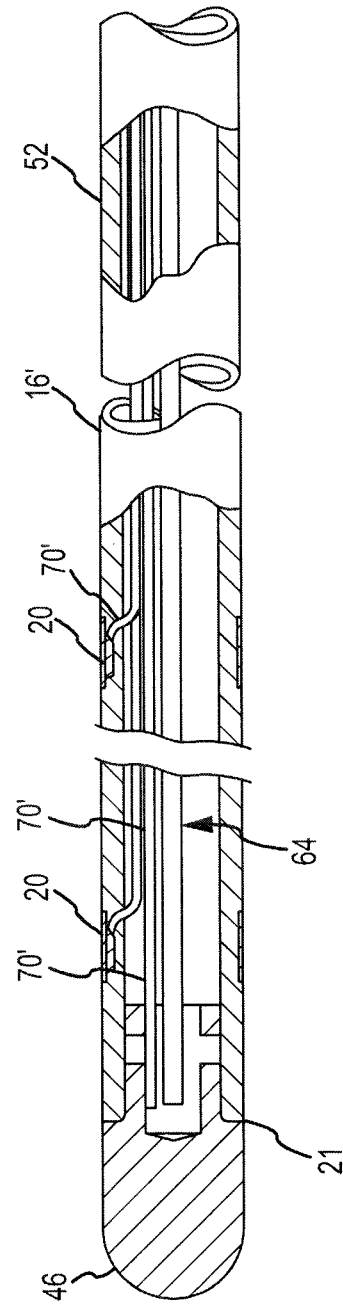
FIG. 4B is an enlarged fragmentary view in partial cross section and partial cut-away of the distal tip electrode and two ring electrodes and flat wire subassembly connection within the catheter body, respectively, shown in FIG. 4A.
Figure 4C:
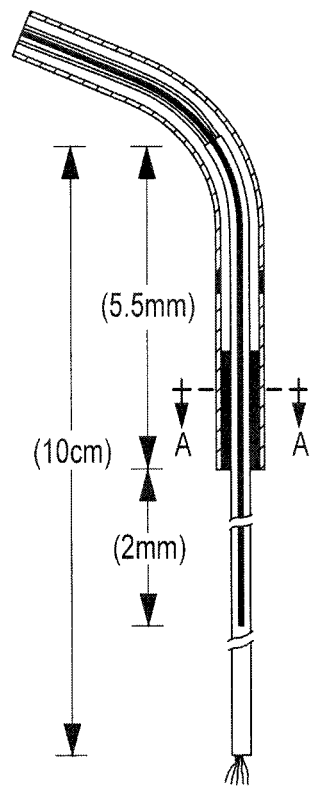
FIG. 4C is an enlarged fragmentary view in partial cross section of the catheter body near the neck region shown in FIG. 4A

FIG. 4A depicts the distal in-plane dual loop cardiac mapping portion 16 of the exemplary EP catheter 10 of FIGS. 1A and 1B (with cross references to details shown in FIGS. 4B and 4C). In the illustrated embodiment the distal portion 16 includes paired twenty pole electrodes 20 with a nominal separation of about 1 mm between each pair of electrodes 20 and 2.5 mm between adjacent pairs of electrodes 20. Of course, other dimensions can be used for the electrodes 20 and the spacing therebetween. At the proximal end of the catheter body 12 a plurality of individually electrically insulated elongate conductors 70 emerge and are adapted to be individually coupled to a mass termination terminal within a handle 72 for ultimate electrical communication with an EP recording system, an electroanatomical localization and visualization system (e.g., such as the ENSITE system of St. Jude Medical, Inc. operating the ONEMAP facility or other similar systems for monitoring cardiac activity and providing one or more visual representations of same).

FIG. 4B is an enlarged fragmentary view in partial cross section and partial cut-away of the distal tip electrode 46 and two ring electrodes 20 and flat wire subassembly 52 connection within the catheter body 12, respectively, shown in FIG. 4A. Each electrode 20,46 couples via an elongate conductor 70' in FIG. 4B to remote EP recording and/or localization and visualization equipment. A biocompatible adhesive 21 (e.g., LOCTITE adhesive) can be applied to the junction of the biocompatible tubing 16 of the distal portion 16 and the electrode 46 to eliminate body fluid ingress therein. A so-called safety wire (or element) 71 can couple to the electrode 46 and a proximal location to reduce or eliminate the chance that the electrode 46 might separate from the catheter assembly 10.

FIG. 4C is an enlarged fragmentary view in partial cross section of the catheter body near the neck region shown in FIG. 4A and indicates a cross sectional view along lines A-A therein which is reflected in FIG. 5 hereinbelow described. The dimensions indicated on FIG. 4C are merely exemplary and illustrative and not intended as limiting in any way.

Figure 5:
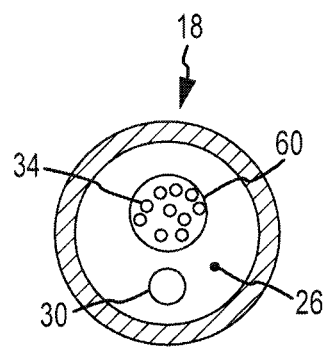
FIG. 5 is a cross-sectional view of the EP catheter illustrated in FIG. 4C taken along line A-A as shown in FIG. 4C.

FIG. 5 is a cross-sectional view of the EP catheter 10 illustrated in FIG. 4C taken along line A-A as shown in FIG. 4C. The biocompatible tubing overlaying next region 18 includes (electrode 20) conductor wires, denoted by reference numeral 34 in FIG. 5, surrounded by polyimide tubing 60 and nominally spaced from nitinol wire 30 by a space impregnated with urethane adhesive 26.

One of ordinary skill in the art will appreciate that electrodes 20 can be ring-type electrodes or any other electrodes suitable for a particular application of EP catheter 10. For example, where EP catheter 10 is intended for use in a contactless EP study, electrodes 20 can be configured as described in U.S. application Ser. No. 12/496,855, filed 2 Jul. 2009, which is hereby incorporated by reference as though fully set forth herein. Of course, in addition to serving sensing purposes (e.g., cardiac mapping and/or diagnosis), electrodes 20 can be employed for therapeutic purposes (e.g., cardiac ablation and/or pacing).

Referring again to the present disclosure in general, various handles and their associated actuators for use in connection with deflecting EP catheters are known, and thus handle 22 will not be described in further detail herein.

In use, EP catheter 10 is introduced into a patient's body proximate an area of interest, such as a pulmonary vein ostium. Of course, EP catheter can be introduced surgically (e.g., via an incision in the patient's chest) or non-surgically (e.g., navigated through the patient's vasculature to a desired site). Activation wire 54 can be actuated in order to deflect proximal region 14 of catheter body 12 such that distal portion 16 is oriented generally towards the ostium of interest. Electrodes 20 can then be employed for diagnostic or therapeutic purposes.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure can be made without departing from the invention as defined in the appended claims.

We claim:

1. An electrophysiology (EP) catheter comprising: a handle; a tubular catheter body having a proximal region, a neck region, and a distal looped region predisposed into at least a dual loop having a majority of said dual loop disposed within a common planar orientation; a flat wire assembly disposed entirely between the handle and the distal looped region, the flat wire assembly having a length of at least about ten centimeters: a first activation wire extending from the handle and terminating within the flat wire assembly; and a plurality of electrodes coupled to the distal looped region; wherein the distal looped region further includes a shape memory material comprising a nickel titanium material or an alloy thereof; wherein the flat wire assembly comprises a segment of flat wire joining the first activation wire and the shape memory material; and wherein the segment of flat wire is flat along its entire length.

2. An EP catheter according to claim 1, wherein said plurality of electrodes includes at least two different types of electrodes, and a one electrode of said plurality of electrodes couples to a distal tip portion of the distal looped region, and wherein a remaining group of electrodes of said plurality of electrodes is of a different type of electrode than said one of said plurality of electrodes.

3. An EP catheter according to claim 2, further comprising a braided structure adjacent the distal looped region.

4. An EP catheter according to claim 3, wherein the handle is configured to impart tension to the first activation wire such that forces acting on the first activation wire are transmitted to the proximal region in order to deflect the catheter body.

5. An EP catheter according to claim 4, wherein the handle further comprises a mass termination terminal for receiving a plurality of electrical conductors.

6. An EP catheter according to claim 2, wherein the looped region comprises at least a dual loop configuration and the plurality of electrodes comprise a plurality of discrete electrodes, between about nine (9) and about nineteen (19), and a distal tip electrode, wherein said distal tip electrode is a different size than said plurality of discrete electrodes.

7. An electrophysiology (EP) catheter, comprising: an elongate catheter body including a proximal region, a distal portion, a neck region joining the distal portion to the proximal region, and wherein the distal portion is configured into at least a full in-plane double-loop with a majority of said full in-plane double-loop sharing a common planar orientation; a handle, said handle coupled to the proximal region of said elongate catheter body; a plurality of electrodes disposed on the distal portion, said plurality of electrodes including at least two different types of electrodes; a flat wire assembly; said flat wire assembly disposed entirely between said handle and said distal portion, including an activation wire disposed within the proximal region of the catheter body and operable to deflect the distal portion of the catheter body via a segment of flat wire, the activation wire extending from the handle, into the flat wire assembly, and terminating short of the distal portion at a connection to the segment of flat wire within a flattened tube, wherein the handle is configured to impart tension to the activation wire such that forces acting on the activation wire are transmitted to the proximal region in order to deflect the catheter body at the segment of flat wire; and a shape memory structure connected to the activation wire via the segment of flat wire within the flattened tube and extending through at least a portion of the distal portion and shaping the portion of the distal portion into at least a full in-plane double-loop; wherein the segment of flat wire is flat along its entire length; and where said flat wire assembly has a length of at least about ten centimeters.

8. An EP catheter according to claim 7, wherein the neck region resides substantially within a central longitudinal axis defined by the proximal region of the catheter body.

9. An EP catheter according to claim 7, wherein the shape memory structure is operable to promote a predefined radius of curvature of the double-loop distal portion.

10. An EP catheter according to claim 7, wherein the handle includes an actuation mechanism operably coupled to the activation wire.

11. An EP catheter according to claim 7, further comprising an adhesive, said adhesive positioned around the flattened tube, the conductor wires, and the segment of flat wire within the tube, wherein said adhesive provides encapsulation properties.

12. An EP catheter according to claim 7, further comprising an adhesive, said adhesive positioned between, above and around an end of the flat wire assembly, wherein said adhesive provides encapsulation properties.

13. An EP catheter according to claim 1, wherein the first activation wire comprises:
 a proximal end originating at the handle;
 a distal end coupled to the segment of flat wire; and
 a middle portion disposed within the tubular catheter body between the proximal and distal ends of the first activation wire.

14. An EP catheter according to claim 1, wherein a distal end of the first activation wire is coupled to a distal region of the segment of flat wire, wherein the distal region of the segment of flat wire terminates short of the dual loop and any of the plurality of electrodes of the distal looped region.

15. An EP catheter according to claim 1, wherein the flat wire assembly further comprises a flattened tube joining the first activation wire and the segment of flat wire.

16. An EP catheter according to claim 15, further comprising a shape memory member extending from the flattened tube and into the dual loop of the distal looped region.

17. An EP catheter according to claim 16, wherein the flat wire assembly further comprises a tube surrounding the segment of flat wire and the flattened tube, and conductor wires extending from the handle to the plurality of electrodes through the tube.

18. An EP catheter according to claim 7, wherein the distal portion is free of activation wires.

19. An EP catheter according to claim 7, wherein the activation wire is not connected to any of the plurality of electrodes.

20. An EP catheter according to claim 7, wherein the activation wire terminates within and is joined to the flat wire assembly.

21. An EP catheter according to claim 1, wherein the neck region transitions an outer diameter of the tubular catheter body from a larger diameter to a smaller diameter at the flat wire assembly.

22. An EP catheter according to claim 21, wherein the transition of the neck region is located just proximal of the dual loop of the distal looped region.

23. An EP catheter according to claim 15, wherein the segment of flat wire anchors the activation wire via the flattened tube, and the flattened tube is located in the neck region, the neck region transitioning an outer diameter of the tubular catheter body from a larger diameter at the proximal region to a smaller diameter at the distal looped region.

24. An EP catheter according to claim 11, wherein the neck region comprises biocompatible tubing that transitions an outer diameter of the tubular catheter body from a larger diameter at the proximal region to a smaller diameter at the distal looped region, wherein the transition of the neck region surrounds the tube and the flattened tube.

* * * * *